US00PP17246P2

(12) United States Plant Patent
van Rijn

(10) Patent No.: US PP17,246 P2
(45) Date of Patent: Nov. 28, 2006

(54) ***ANTHURIUM* PLANT NAMED 'RIJN200310'**

(50) Latin Name: *Anthurium andreanum*
Varietal Denomination: Rijn200310

(75) Inventor: Leonardus W. B. M. van Rijn, De Lier (NL)

(73) Assignee: Rijn Plant BV, De Lier (NL)

( * ) Notice: Subject to any disclaimer, the term of this patent is extended or adjusted under 35 U.S.C. 154(b) by 0 days.

(21) Appl. No.: 11/236,974

(22) Filed: Sep. 28, 2005

(51) Int. Cl.
*A01H 5/00* (2006.01)

(52) U.S. Cl. ..... Plt./365
(58) Field of Classification Search ..... Plt./365
See application file for complete search history.

*Primary Examiner*—Kent Bell

(57) ABSTRACT

A new cultivar of *Anthurium* plant named 'Rijn200310' that is characterized by an upright and outwardly spreading habit, dark green leaves, free flowering, red spathes positioned above the foliage on strong erect scapes, long inflorescence life, large spathe size and white and yellow colored spadices.

1 Drawing Sheet

Botanical classification: *Anthurium andreanum.*
Variety denomination: 'Rijn200310'.

BACKGROUND OF THE INVENTION

The present invention relates to a new and distinct cultivar of *Anthurium* plant botanically known as *Anthurium andreanum* and hereinafter referred to by the cultivar name 'Rijn200310'.

'Rijn200310' is a hybrid that originated from the hybridization of the female or seed parent a proprietary *Anthurium* identified as 9513 (not patented) and the male or pollen parent a proprietary *Anthurium* identified as 9701 (not patented). The cultivar 'Rijn200310' was selected by the inventor in February of 2003 as a single plant within the progeny of the stated cross in De Lier, The Netherlands.

Asexual reproduction by tissue culture of the new cultivar 'Rijn200310' was first performed in May of 2003 in Melsen-Merelbeke, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Anthurium* cultivar 'Rijn200310'.

1. *Anthurium* 'Rijn200310' exhibits an upright and outwardly spreading habit.
2. *Anthurium* 'Rijn200310' exhibits dark green leaves.
3. *Anthurium* 'Rjin200310' exhibits free flowering.
4. *Anthurium* 'Rijn200310' exhibits red spathes positioned above the foliage on strong erect scapes.
5. *Anthurim* 'Rijn200310' exhibits long inflorescence life.
6. *Anthurium* 'Rijn200310' exhibits a large spathe size.
7. *Anthurium* 'Rijn200310' exhibits white and yellow colored spadices.

The closest comparison cultivar is *Anthurium* 'Rijn200002' (not patented). The new cultivar 'Rijn200310' is distinguishable from 'Rijn200002' by the following characteristics:

1. 'Rijn200310' has smaller leaves than 'Rijn200002'.
2. 'Rijn200310' has larger spathes than 'Rijn200002'.

The new cultivar 'Rijn200310' is distinguishable from the male parent *Anthurium* 9701 in having thinner leaves and spathes and a spathe color that is less red.

The new cultivar 'Rijn200310' is distinguishable from the female parent *Anthurium* 9513 in having smaller leaves and spathes that are orange.

BRIEF DESCRIPTION OF THE DRAWING

The accompanying photograph illustrates the distinguishing traits of *Anthurium* 'Rijn200310'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Anthurium* cultivar named 'Rijn200310'. Data was collected in De Lier, The Netherlands from 24 month old greenhouse grown plants in 21 cm containers. The time of year was Summer and the average temperature was 23 degrees Centigrade during the day and 21 degrees Centigrade at night. No photoperiodic treatments or growth retardants were used. Color determinations are in accordance with The Royal Horticultural Society Chart 2001 edition, except where general color terms of ordinary dictionary significance are used. The growing requirements are similar to the species. 'Rijn200310' has not been tested under all possible conditions and phenotypic differences may be observed with variations in environmental, climatic, and cultural conditions, however, without any variance in genotype.

Botanical classification: *Anthurium andreanum* 'Rijn200310'.
Use: Ornamental.
Parentage: 'Rijn200310' is a hybrid plant that resulted from the hybridization of the following parent plants:

*Female parent.*—A proprietary *Anthurium* identified as 9513.

*Male parent.*—A proprietary *Anthurium* identified as 9701.

Vigor: Moderate.
Growth rate: Moderate.
Growth habit: Moderately branching from base, busy and dense.
Plant shape: Inverted triangle with inflorescences on top.
Suitable container size: 14 cm diameter container.
Height: Average 49 cm to top of leaf plane, 64 cm to top of inflorescences.
Width: Average 66 cm. in width.
Hardiness: USDA Zone 10.
Propagation: Tissue Culture.
Time to initiate roots (summer and winter): Approximately 28 days to produce roots on an initial cutting.
Time to produce a rooted cutting or liner (summer and winter): Approximately 270 days.
Root system: Fine and fibrous.
Stem:
*Average number of stems.*—5.
*Stem appearance.*—Stems very short.
*Stem length.*—0.2 cm.
*Stem diameter.*—0.9 cm.
*Internode length.*—1 mm.
*Stem aspect.*—Glabrous.
*Stem strength.*—Strong.
*Stem color* (*immature*).—N199C.
*Stem color* (*mature*).—N199B.
Foliage:
*Texture.*—Smooth.
*Leaf arrangement.*—Alternate.
*Compound or single.*—Single.
*Leaf shape.*—Narrow cordate.
*Leaf apex.*—Apiculate.
*Leaf base.*—Cordate.
*Leaf length.*—Average 29.6 cm in length.
*Leaf width.*—15.2 cm in width.
*Quantity of leaves per clump.*—Average 3.
*Pubescence.*—Absent.
*Leaf margin.*—Entire.
*Vein pattern.*—Pinnate.
*Young leaf color* (*upper surface*).—141A to 147A.
*Young leaf color* (*lower surface*).—148A.
*Mature leaf color* (*upper surface*).—137A to 147A.
*Mature leaf color* (*lower surface*).—144A.
*Vein color* (*lower surface*).—144A.
*Vein color* (*upper surface*).—143B.
*Leaf attachment.*—Petiolate.
*Petiole dimensions.*—Average 28.9 cm in length excluding geniculum, 4 mm in diameter below geniculum to 6.5 mm in diameter above clump.
*Petiole aspect.*—Round.
*Petiole color.*—143A.
*Geniculum dimensions.*—Average 2.8 cm in length and 5 mm in diameter.
*Geniculum aspect.*—Rounded, slightly glossy, glabrous.
*Geniculum color.*—143A.
*Wing length.*—5.7 cm.
*Wing diameter.*—5 mm.
*Wing color.*—144A, tinged 181C.
*Petiole sheath dimensions.*—Average 12.2 cm in length and 9 mm in diameter.
*Petiole sheath color.*—178A to 178B.
*Durability of foliage to stress.*—High.
Inflorescence:
*Inflorescence arrangement: Spathes with spadices held above and beyond the foliage, flowering structures arise from leaf-axils.*
*Flowering habit: Continuous.*
*Quanity of spathes per plant.*—Average 8.
*Natural flowering season.*—Autumn.
*Time to flower or response time.*—8 months.
*Fragrance.*—Absent.
*Longevity.*—3 months in summer, 2 months in winter.
*Self-cleaning or persistent.*—Persistent.
*Spathe aspect.*—Cupped.
*Spathe dimensions.*—Average 14.5 cm in length, 12.5 cm in width.
*Spathe texture.*—Glabrous, slightly leathery.
*Spathe shape.*—Reniform.
*Spathe margin.*—Entire.
*Spathe apex.*—Acute.
*Spathe color when opening* (*front side*).—46B.
*Spathe color when opening* (*back side*).—45A.
*Spathe color when fully opened* (*front side*).—46A.
*Spathe color when fully opened* (*back side*).—45B.
*Spathe color fading to.*—53A.
*Spadix shape.*—Columnar.
*Spadix tip.*—Obtuse.
*Spadix base.*—Obtuse.
*Spadix dimensions.*—Average 7.4 cm in length and 1 cm in diameter.
*Spadix color when opening.*—21A to 22A.
*Spadix color when fully opened.*—11D.
*Quantity of flowers per spadix.*—Average 300.
*Spadix flower arrangement.*—Bisexual, rounded in cross-section, single.
*Spadix flower dimensions.*—1 mm in diameter and less than 0.5 mm in depth.
Reproductive organs:
*Anther color.*—155B.
*Amount of pollen.*—Low.
*Pollen color.*—155B.
*Stigma color.*—155D.
*Ovary color.*—155D.
Peduncle:
*Peduncle dimensions.*—Average 56.7 cm in length and 6 mm. in diameter.
*Peduncle angle.*—5 degrees relative to the stem.
*Peduncle color.*—144A.
*Peduncle strength.*—Strong.
Seed: Seed production has not been observed.
Disease and insect resistance: Plants of the new *Anthurium* have not been observed for disease or insect resistance.

It is claimed:

1. A new and distinct variety of *Anthurium* plant named 'Rijn200310' as described and illustrated.

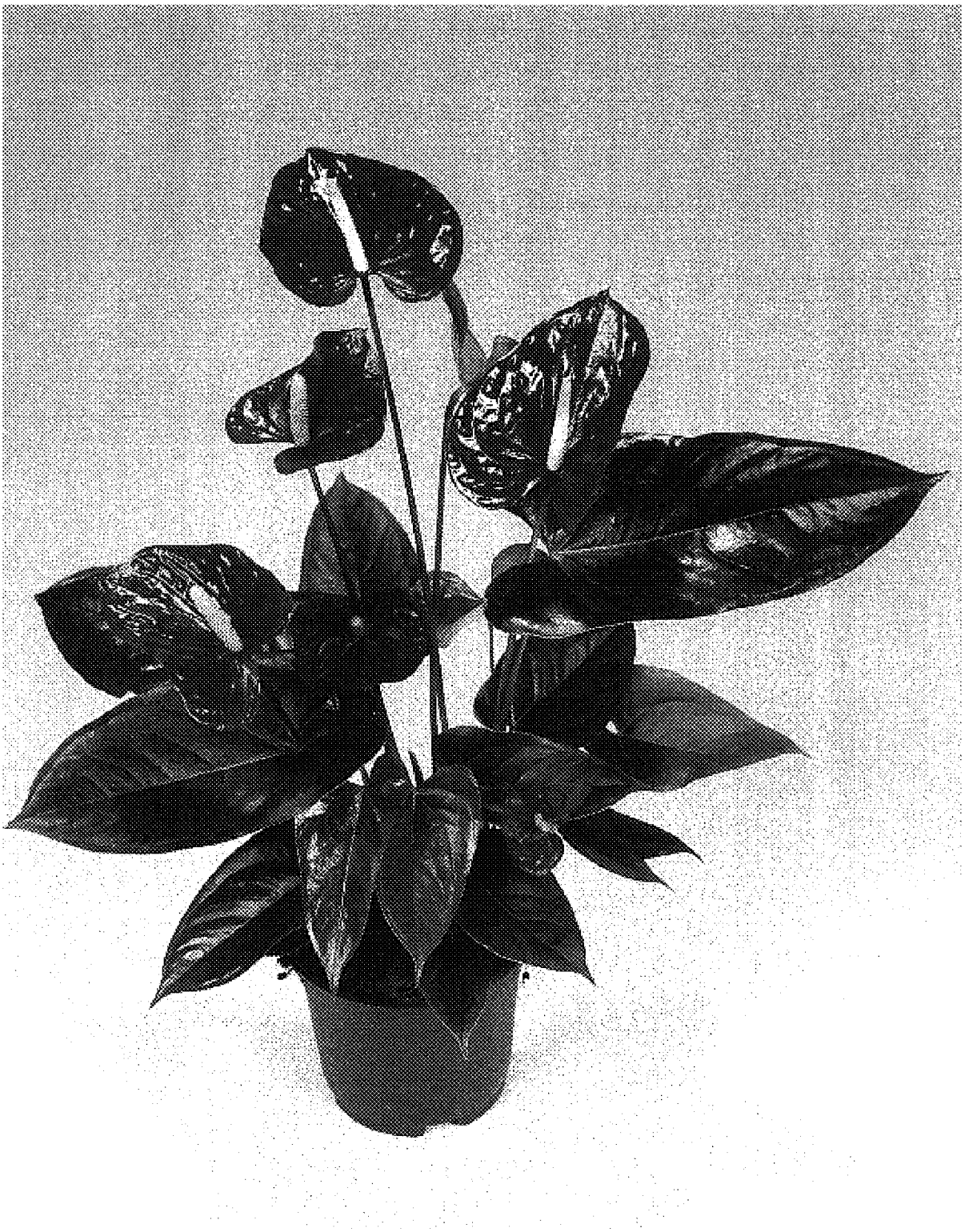

* * * * *